(12) United States Patent
Kim et al.

(10) Patent No.: US 7,611,888 B2
(45) Date of Patent: Nov. 3, 2009

(54) ROTAXANE COMPOUND, ROTAXANE-BONDED SOLID SUBSTRATE, AND BIOCHIP USING THE SAME

(75) Inventors: Kimoon Kim, Pohang (KR); Jin Koo Kang, Pohang (KR); Woo Seong Jeon, Pohang (KR); Miran Noh, Pohang (KR); Dongwoo Kim, Pohang (KR); Kangkyun Baek, Pohang (KR)

(73) Assignee: Postech Foundation, Pohang (KR)

( * ) Notice: Subject to any disclaimer, the term of this patent is extended or adjusted under 35 U.S.C. 154(b) by 249 days.

(21) Appl. No.: 10/563,477

(22) PCT Filed: Jul. 5, 2004

(86) PCT No.: PCT/KR2004/001651

§ 371 (c)(1),
(2), (4) Date: Jan. 5, 2006

(87) PCT Pub. No.: WO2005/003136

PCT Pub. Date: Jan. 13, 2005

(65) Prior Publication Data

US 2006/0154254 A1 Jul. 13, 2006

(30) Foreign Application Priority Data

Jul. 5, 2003 (KR) .................. 10-2003-0045522

(51) Int. Cl.
| | |
|---|---|
| C12M 1/34 | (2006.01) |
| G01N 33/552 | (2006.01) |
| C07K 1/10 | (2006.01) |
| C12Q 1/68 | (2006.01) |
| G01N 33/53 | (2006.01) |
| C07D 245/00 | (2006.01) |

(52) U.S. Cl. .................. 435/287.2; 435/6; 435/7.92; 436/528; 530/402; 540/460; 564/281; 564/282; 564/291

(58) Field of Classification Search .............. 435/7.92, 435/287.2; 436/527; 530/409; 540/460; 564/281, 282, 291
See application file for complete search history.

(56) References Cited

FOREIGN PATENT DOCUMENTS

KR 1020010039662 A 5/2001

(Continued)

OTHER PUBLICATIONS

Lee et al. A two-dimentional polyrotaxane with large cavities and channels: a novel approach to metal-organic open-frameworks by using supramolecular building blocks. Angew. Chem. Int. Ed. 2001, Vpl. 40, No. 2, pp. 399-402.*

(Continued)

*Primary Examiner*—Shafiqul Haq
(74) *Attorney, Agent, or Firm*—Rothwell, Figg, Ernst & Manbeck, PC

(57) ABSTRACT

The present disclosure provides a rotaxane compound that can be used to separate molecules within a linkage layer formed on a solid substrate of a biochip by a predetermined distance. The compound is represented by Formula 1, in which a compound of Formula 3 vertically passes through a cavity of cucurbituril or its derivative of Formula 2. It further provides gene chips, protein chips and sensors for biomaterial assays which use the rotaxane molecules to allow biomaterials to be immobilized on a linkage layer such that they are regularly spaced apart from each other by a predetermined distance.

10 Claims, 6 Drawing Sheets

FOREIGN PATENT DOCUMENTS

| | | | |
|---|---|---|---|
| KR | 1020020019325 A | 3/2002 |
| KR | 1020030003901 A | 1/2003 |
| KR | 1020030024426 A | 3/2003 |
| KR | 1020030060053 A | 7/2003 |

OTHER PUBLICATIONS

Levicky, R., et al., "Using Self-Assembly to Control the Structure of DNA Monolayers on Gold: A Neutron Reflectivity Study", J. Am. Chem. Soc. 1998, 120, pp. 9787-9792.

Peterson, A.W., et al., "Hybridization of Mismatched or Partially Matched DNA at Surfaces", Nov. 15, 2002, JACS Articles, J. Am. Chem. Soc., 124, 14601-14607.

Hong, B.J., et al., "Self-Assembly of a Dendron through Multiple Ionic Interaction to Give Mesospacing Between Reactive Amine Groups on the Surface", Langmuir, 2003, 19, pp. 2357-2365.

Supplementary European Search Report issued in EP 04774077 dated Jan. 19, 2009, 3 pages.

H. Isobe, et al.: "Ternary Complexes Between DNA, Polyamine, and Cucurbituril: A Modular Approach to DNA-Binding Molecules," Angewandte Chemie, International Edition, 39(23), 2000, pp. 4257-4260, XP008064000.

H. Buschmann, et al.: "Synthesis of cucurbituril-spermine-[2]rotaxanes of the amide-type," retrieved from STN Database accession No. 2000:311143, abstract & Supramolecular Chemistry, 11(3), 225-231, Coden: Scheer; ISSN: 1061.2078, 2000, 3 pages, XP002510812.

Database Crossfire Beilstein, Beilstein Institut Zur Foerderung Der Chemischen Wissenschaften, Frankfurt Am Main, DE, Database accession No. 7558843, abstract & Chemistry Letters, vol. 7, 1996, 1 page, XP002510813.

D. Whang, et al.: "Self-Assembly of a Polyrotaxane Containing a Cyclic "Bead" in Every Structural Unit in the Solid State: Cucurbituril Molecules Threaded on a One-Dimensional Coordination Polymer," Journal of the Amnerican Chemical Society, 118(45), 1996, pp. 11333-11334, XP002510810.

J. Wook Lee, et al.: "A kinetically controlled molecular switch based on bistable [2]rotaxane," Chemical Communications (Cambridge, United Kingdom), (11), 2001, pp. 1042-1043, XP002510811.

\* cited by examiner

US 7,611,888 B2

ROTAXANE COMPOUND, ROTAXANE-BONDED SOLID SUBSTRATE, AND BIOCHIP USING THE SAME

CROSS REFERENCE TO RELATED APPLICATION

This application is a 35 U.S.C. § 371 National Phase Entry Application from PCT/KR2004/001651, filed Jul. 5, 2004, and designating the U.S.

BACKGROUND OF THE INVENTION

1. Field of the Invention

The present invention relates to a solid substrate for a biochip having a uniform spacing of predetermined functional groups and a biochip using the same. More particularly, the present invention relates to a rotaxane compound, a rotaxane compound-bonded solid substrate, and a biochip using the solid substrate.

2. Description of the Related Art

Generally, to introduce a compound to a solid substrate, a method as illustrated in FIG. 1 is widely used. According to this method, on a solid substrate 1, there is formed a self-assembled thin film made of a silane compound or a thiol compound, an end of which has a functional group 2a for a linkage with the solid substrate 1 and the other end has a functional group 2c for a linkage with a compound to be introduced to the solid substrate 1. In the formation of the self-assembled thin film, molecular bodies, which are represented by a reference numeral 2b in FIG. 1, serve to increase the density of the thin film formed by molecular interaction therebetween. When the molecular bodies 2b are linear alkyl groups which are the simplest molecular structures, intermolecular spacing in a thin film formed therefrom is known to be about 0.5 nm.

As is well known, when a silane compound or a thiol compound with an additional end functional group is formed as a thin film on a specific solid substrate, chemical species, such as biomaterials, polymers, or nanoparticles, including DNAs and proteins, which are difficult to be immobilized on a solid substrate when used alone, can be easily and uniformly immobilized on the solid substrate. Therefore, many recent studies have been focused on immobilization of target compounds on solid substrates using such a silane compound or thiol compound.

Among these studies, in particular, a biochip technology for detection and assay of biomaterials, including DNAs and proteins, has been actively studied because it allows for the quick analysis of an interaction between a large number of biomaterials. In this regard, developments of techniques for the preparation of biochips with excellent sensitivity and selectivity have been competitively carried out.

A biochip includes a solid substrate 1 (a support layer) such as a silicon substrate or a glass substrate, a molecule layer (a linkage layer 2) formed on the solid substrate and having an end functional group that can be chemically bonded with DNA or protein, and a biomaterial layer (a detection layer 3) having DNA (complementary DNA) or protein that can selectively interact with a target material to be assayed, as shown in FIG. 2. Such a biochip is generally prepared as a pattern shape, like 1 of FIG. 3, and is then subjected to serial processes 7 and 8 to detect a target material to be assayed, which is well known in ordinary persons skilled in the art. In FIG. 3 is a solid substrate, 2 is a linkage layer, 3 is a detection layer (DNA single strand), 5 is a hybridized DNA double strand, 7 is sample insertion and DNA hybridization, and 8 is detection.

As shown in FIG. 4, when biomaterials, such as DNAs or proteins, which are immobilized on the solid substrate 1, selectively interact with specific target materials, they may be changed in structure or volume, in particular, toward a specific three-dimensional structure, which is well known in the pertinent art. In particular, in a case where biomaterials immobilized on the solid substrate 1 of the biochip are DNAs, a maximal cross-sectional diameter of DNA single strands immobilized on the detection layer 3 is about 1 nm or less. However, when the DNA single strands are hybridized with target DNA strands present in a sample to form double strand structures, a maximal cross-sectional diameter of the double strand structures is about 2.2 nm, which is larger than the maximal cross-sectional diameter of the DNA single strands. In FIG. 4 is a solid substrate, 2 is a linkage layer, 3 is a detection layer (DNA single strand), 5 is a hybridized DNA double helix, 7 is sample insertion and DNA hybridization.

It has been known that currently available DNA chip preparation technology has a limitation in presetting the spacing between DNA single strands used as the detection layer considering a size change that may result from hybridization with target DNA strands. If the DNA single strands are excessively densely spaced, the target DNA strands present in a sample cannot enter the detection layer due to a steric hindrance, which renders formation of double strand structures by hybridization with the DNA single strands immobilized on a solid substrate difficult. On the other hand, excessively sparse spacing of the DNA single strands on the solid substrate may lower the sensitivity of a DNA chip.

Hitherto, although a DNA chip has been mainly illustrated, there may arise similar problems to the above in a biochip except a DNA chip. For the forgoing reasons, an increase of the concentration of biomaterials constituting a detection layer per unit area alone cannot prepare a biochip with excellent selectivity and sensitivity. Rather, it is necessary to optimally space biomaterials of a detection layer to ensure constant sensitivity and selective interaction.

DNA double strands obtained by hybridization between target DNA strands and DNA strands immobilized on a solid substrate have a cross-sectional diameter that is about twice larger than the DNA strands immobilized on the solid substrate. In this regard, if DNA strands are excessively densely immobilized on a solid substrate of a DNA chip, steric hindrance may occur during subsequent hybridization with target DNA strands, thereby decreasing the efficiency of the DNA chip, as shown in (a) of FIG. 5 below. Therefore, to prepare a DNA chip with excellent selectivity and sensitivity, when DNA strands are immobilized on a solid substrate 1 to form a detection layer 3, the DNA strands must have uniform and close spacing considering a change in structure or volume that may be caused in subsequent hybridization, as shown in (b) of FIG. 5. In FIG. 5 is a solid substrate, 2 is a linkage layer, 3 is a detection layer (DNA single strand), and 6 is a target DNA strand.

The above-described steric hindrance problem that may be caused due to the structural change of biomaterials immobilized on a solid substrate during detection may also occur in a protein chip in which the sizes of proteins immobilized on a solid substrate are not large enough compared to those of target molecules (counterpart molecules selectively bonded with the proteins immobilized on the solid substrate), in addition to a DNA chip. For example, this may also be caused in a case where macromolecules, such as avidin, are bonded to micromolecules, such as biotin, immobilized on a solid substrate, which is widely used in a protein chip. Furthermore, the steric hindrance problem may also be caused at all chips in which chemical materials immobilized on a solid substrate are bonded to target materials, in addition to a biochip such as a DNA chip and a protein chip.

The best solution for this problem is to appropriately adjust the density of a linkage layer formed on a solid substrate. By doing so, the spacing between DNAs or proteins within a detection layer formed on the linkage layer can be adjusted.

Generally, the density of the linkage layer can be adjusted by controlling the concentration of a linkage layer material and the duration for linkage layer formation. Tarlov et al. reported a study in which adjustment of the concentration of a self-assembled thin film (corresponding to a linkage layer) material enables a change in spacing between chemical species [J. Am. Chem. Soc. 1998, 120, 9787]. According to this method, however, it is impossible to form a linkage layer with a uniform density distribution, which makes it difficult to control the spacing between DNAs formed on the linkage layer to a desired level. Recently, Georgiadis et al. reported a quantitative study measuring the degree of hybridization of DNAs after adjusting the spacing between chemical species by the same method as Tarlov et al. method. However, the above-described problem still remained [J. Am. Chem. Soc. 2002, 124, 14601].

Recently, Jun-Won Park and co-workers reported a method for adjusting the spacing between compounds used for a detection layer using conical dendron molecules [Korean Patent Laid-Open Publication No. 2002-0019325; Langmuir 19, 2003, p. 2357]. According to this method, when an aminosilane-modified solid substrate is treated with the dendron molecules, the lower end of each of which has 10 carboxyl groups and the upper end has a single amine group, a hydrogen bond between amine groups of the surface of the solid substrate and carboxyl groups of the lower ends of the dendron molecules occurs. Therefore, the dendron molecules are immobilized on the solid substrate and the amine groups present on the upper ends of the dendron molecules are spaced correspondingly to the maximal cross-sectional diameter of the dendron molecules. However, due to structural fragility, the dendron molecules may be easily changed structurally, such as bending or folding by rotation of a single bond, thereby reducing the spacing between the amine groups. Furthermore, overlapping of the dendron molecules may reduce the spacing between the amine groups. In this regard, this method cannot completely remove disadvantages caused by conventional methods. In addition, since the dendron molecules used in this method have a large number of functional groups, nonspecific binding occurrence which inhibits the performance of a DNA chip or a protein chip may increase.

SUMMARY OF THE INVENTION

The present invention provides a rotaxane compound for constituting a linkage layer formed on a solid substrate in which constitutive molecules within the linkage layer are spaced apart from each other by a predetermined distance.

The present invention also provides a rotaxane compound-bonded solid substrate.

The present invention also provides a gene chip and a protein chip, each of which includes a rotaxane compound-bonded solid substrate.

The present invention also provides a sensor for biomaterial assay including a rotaxane compound-bonded solid substrate.

According to an aspect of the present invention, there is provided a rotaxane compound represented by Formula 1 below in which a compound of Formula 3 below vertically passes through a cavity of cucurbituril or its derivative of Formula 2 below:

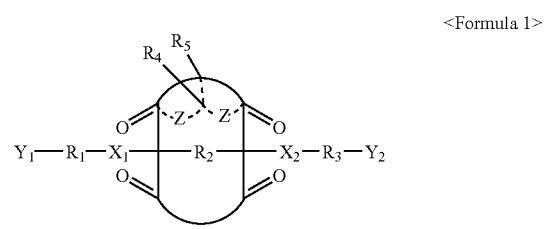

<Formula 1> wherein R1, R2, and R3 are each independently saturated or unsaturated linear C2-C10 alkylene, ethyleneglycol oligomer, 1,4-substituted benzene, or 1,4-substituted pyridine; X1 and X2 are each independently a positively charged functional group for ion-dipole interaction with an oxygen atom of cucurbituril or its derivative of Formula 2; Y1 is a functional group for a linkage with a biomaterial including a gene or a protein; and Y2 is a functional group for a linkage with a solid substrate,

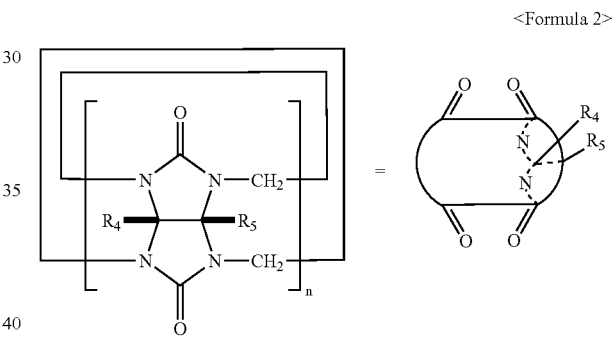

<Formula 2> wherein n is an integer of 4 to 20; and R4 and R5 are each independently hydrogen, an alkenyloxy group with an unsaturated bond end and a substituted or unsubstituted alkyl moiety of C1-C20, a carboxyalkylsulfinyloxy group with a substituted or unsubstituted alkyl moiety of C1-C20, a carboxyalkyloxy group with a substituted or unsubstituted alkyl moiety of C2-C8, an aminoalkyloxy group with a substituted or unsubstituted alkyl moiety of C2-C8, or a hydroxyalkyloxy group with a substituted or unsubstituted alkyl moiety of C2-C8, and

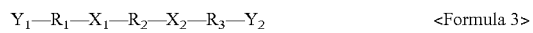

<Formula 3> wherein $R_1$, $R_2$, $R_3$, $X_1$, $X_2$, $Y_1$, and $Y_2$ are as defined in Formula 1 above.

In the rotaxane compound of Formula 1, $X_1$ and $X_2$ may be each independently secondary ammonium, 1,4-substituted pyridinum, or benzyl ammonium; and $Y_1$ and $Y_2$ may be each independently a primary amine group, an amide group, an acrylamine group, an alkylester group, an aldehyde group, a carboxyl group, an alkoxysilane group, a halogenated acyl group, a hydroxyl group, a thiol group, a halogen group, a cyan group, an isocyan group, or an isothiocyan group.

According to another aspect of the present invention, there is provided a solid substrate bonded with a compound of Formula 1 via a covalent bond or a non-covalent bond.

The compound of Formula 1 may be bonded to the solid substrate in a density of 0.05 to 0.6 compounds/nm2.

The solid substrate may be a glass, a silicon wafer, an indium tin oxide (ITO) glass, an aluminum oxide substrate, or a titanium dioxide substrate.

According to another aspect of the present invention, there is provided a gene chip including a solid substrate bonded with a compound of Formula 1.

According to another aspect of the present invention, there is provided a protein chip including a solid substrate bonded with a compound of Formula 1.

According to another aspect of the present invention, there is provided a sensor for biomaterial assay including a solid substrate bonded with a compound of Formula 1.

BRIEF DESCRIPTION OF THE DRAWING

The above and other features and advantages of the present invention will become more apparent by describing in detail exemplary embodiments thereof with reference to the attached drawing in which.

DETAILED DESCRIPTION OF THE INVENTION

Hereinafter, the present invention will be described in detail.

Figure 1:
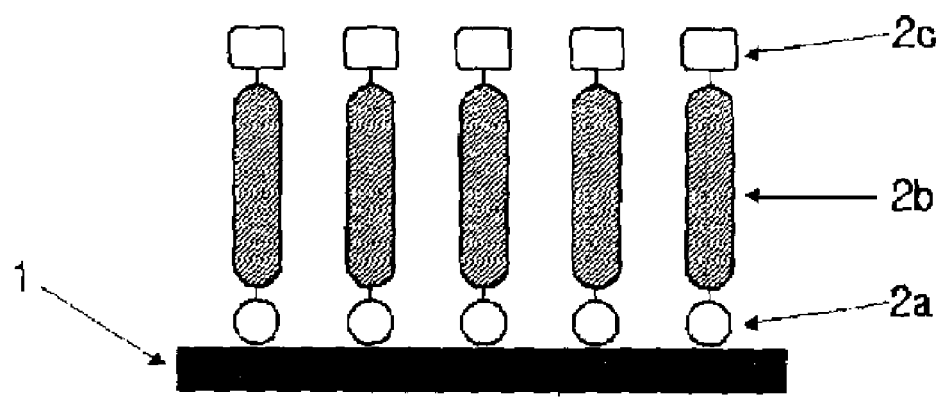
FIG. 1 is a diagram showing self-assembled thin film made of a silane compound or a thiol compound, an end of which has a functional group for a linkage with the solid substrate and the other end has a functional group for a linkage with a compound to be introduced to the solid substrate.
Figure 2:
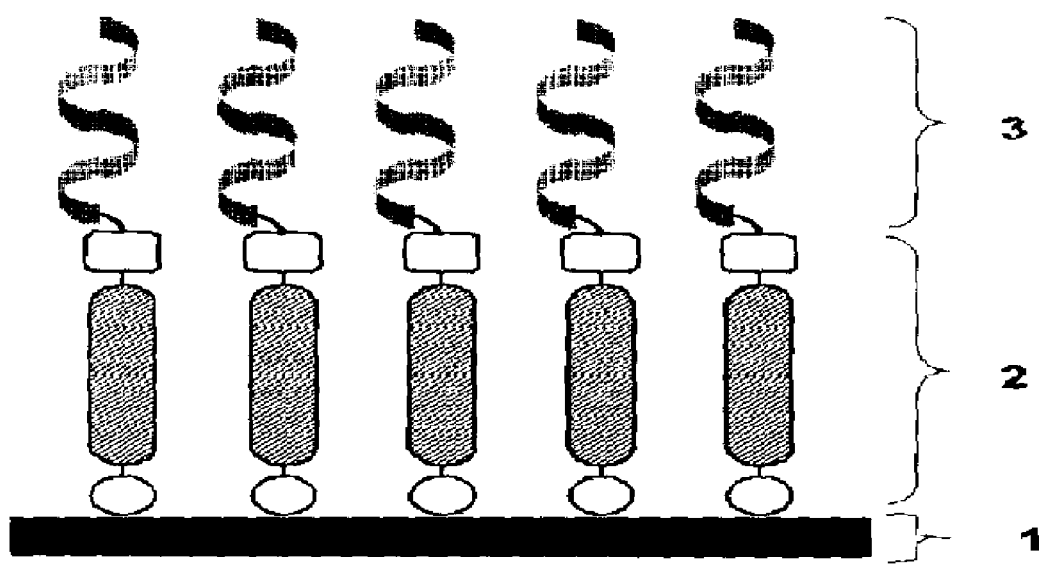
FIG. 2. is a diagram showing a biochip including a solid substrate (a support layer) such as a silicon substrate or a glass substrate, a molecule layer (a linkage layer) formed on the solid substrate and having an end functional group that can be chemically bonded with DNA or protein, and a biomaterial layer (a detection layer) having DNA (complementary DNA) or protein that can selectively interact with a target material to be assayed.
Figure 3:
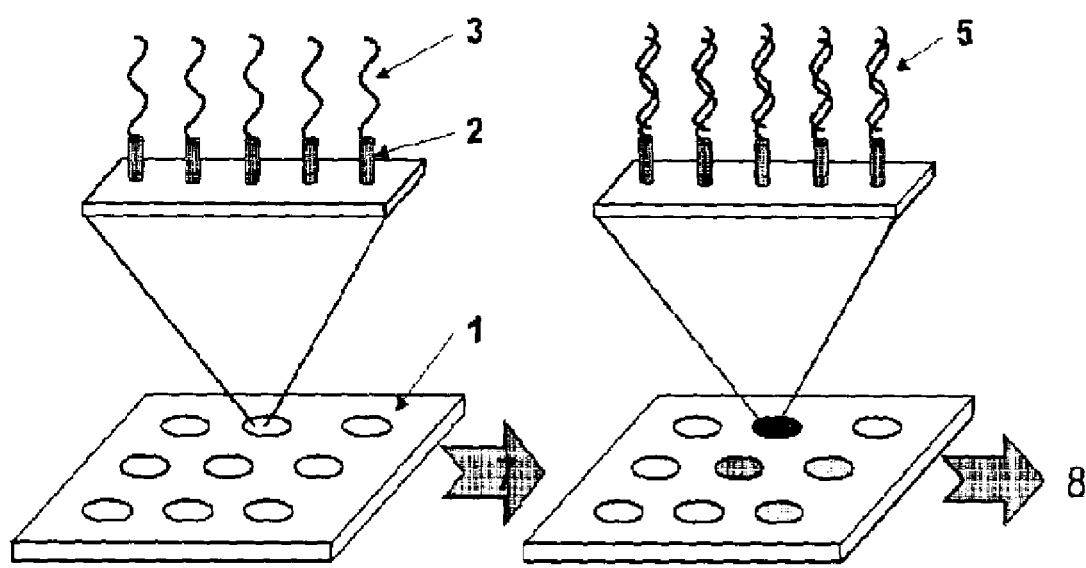
FIG. 3 is a diagram showing that a biochip is generally prepared as a pattern shape, and is then subjected to serial processes to detect a target material to be assayed, which is well known in ordinary persons skilled in the art.
Figure 4:
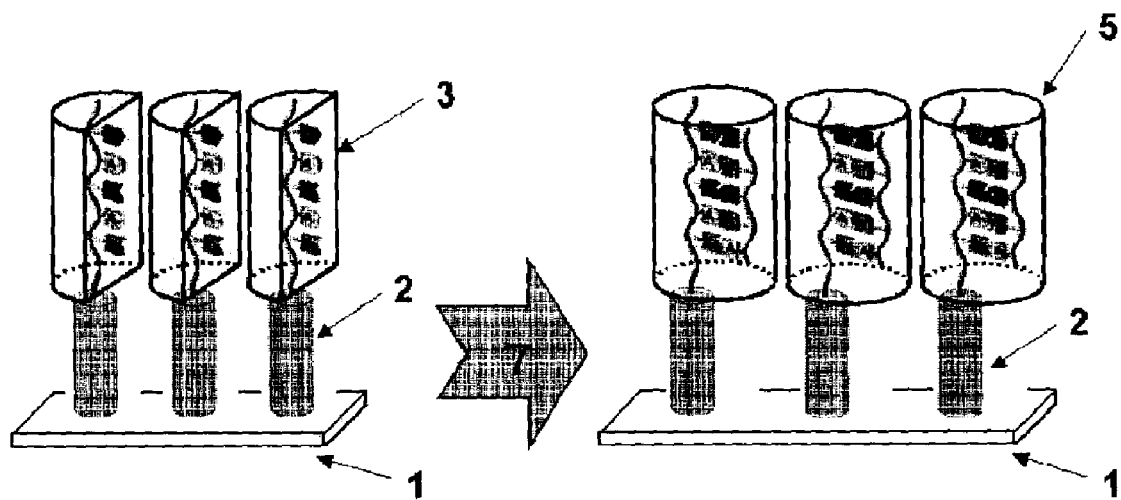
FIG. 4. is a diagram showing that when biomaterials, such as DNAs or proteins, which are immobilized on the solid substrate, selectively interact with specific target materials, they may be changed in structure or volume, in particular, toward a specific three-dimensional structure, which is well known in the pertinent art.
Figure 5:
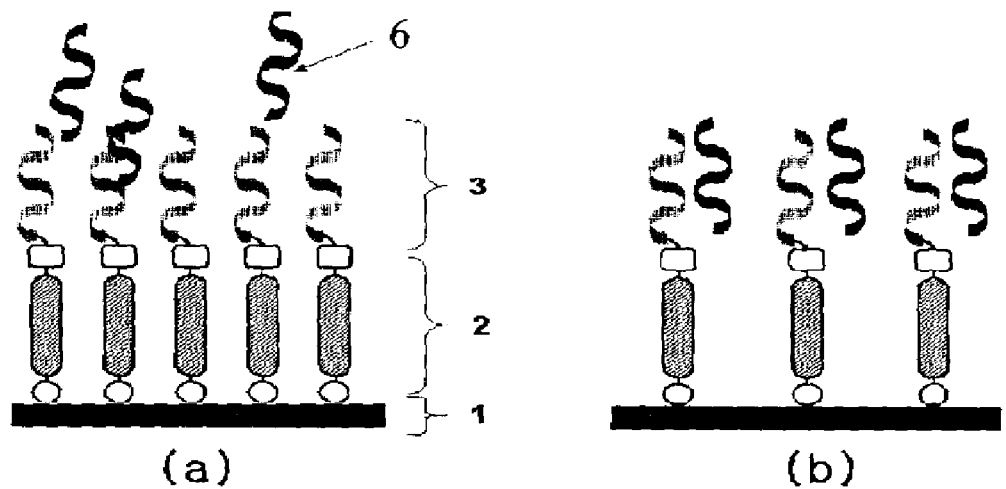
FIG. 5 is a diagram showing that if DNA strands are excessively densely immobilized on a solid substrate of a DNA chip, steric hindrance may occur during subsequent hybridization with target DNA strands, thereby decreasing the efficiency of the DNA chip, as shown in (a) and thus, when DNA strands are immobilized on a solid substrate to form a detection layer, the DNA strands must have uniform and close spacing considering a change in structure or volume that may be caused in subsequent hybridization, as shown in (b)
Figure 6:
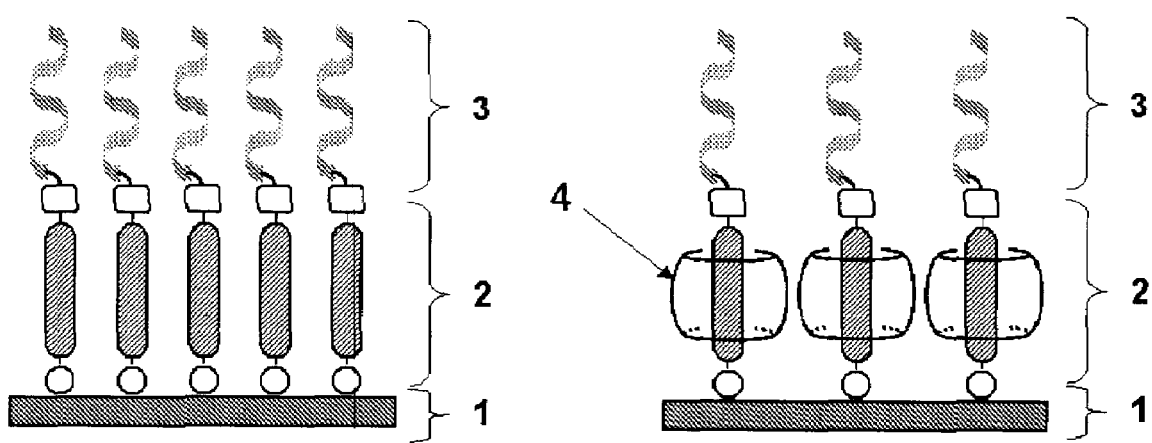
FIG. 6 is a diagram that illustrates a solid substrate bonded with a linkage layer made of rotaxane molecules in which elongated linear compounds vertically pass through cavities of cucurbituril or its derivatives, and a principle that the molecules which constitute the linkage layer are spaced apart from each other by a distance corresponding to more than a diameter of cucurbituril or its derivatives.

According to the present invention, a rotaxane compound is used to separate molecules within a linkage layer formed on a solid substrate of a biochip by a predetermined distance. As used herein, the term "rotaxane compound" refers to an interlocked compound in which an elongated linear compound threads through cucurbituril which is a rigid cyclic compound. When such a rotaxane compound is introduced in a linkage layer, the spacing between adjacent linear compounds can be maintained at more than a diameter of cucurbituril. Based on this principle, when a linkage layer made of a rotaxane compound is formed on a solid substrate, molecules which constitute the linkage layer can be spaced apart from each other by a predetermined distance. This principle is shown in FIG. 6.

Therefore, the present invention provides a rotaxane compound represented by Formula 1 below in which a compound of Formula 3 below threads through cucurbituril or its derivative of Formula 2 below:

<Formula 1>

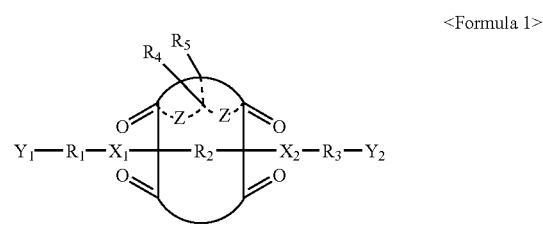

wherein R1, R2, and R3 are each independently saturated or unsaturated linear C2-C10 alkylene, ethyleneglycol oligomer, 1,4-substituted benzene, or 1,4-substituted pyridine; X1 and X2 are each independently a positively charged functional group for ion-dipole interaction with an oxygen atom of cucurbituril or its derivative of Formula 2; Y1 is a functional group for a linkage with a biomaterial including a gene or a protein; and Y2 is a functional group for a linkage with a solid substrate, <Formula 2>

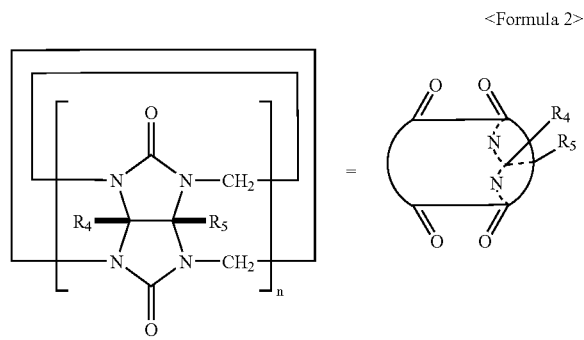

wherein n is an integer of 4 to 20; and $R_4$ and $R_5$ are each independently hydrogen, an alkenyloxy group with an unsaturated bond end and a substituted or unsubstituted alkyl moiety of $C_1$-$C_{20}$, a carboxyalkylsulfinyloxy group with a substituted or unsubstituted alkyl moiety of $C_1$-$C_{20}$, a carboxyalkyloxy group with a substituted or unsubstituted alkyl moiety of $C_2$-$C_8$, an aminoalkyloxy group with a substituted or unsubstituted alkyl moiety of $C_2$-$C_8$, or a hydroxyalkyloxy group with a substituted or unsubstituted alkyl moiety of $C_2$-$C_8$, and $$Y_1—R_1—X_1—R_2—X_2—R_3—Y_2 \quad \text{<Formula 3>}$$

wherein $R_1$, $R_2$, $R_3$, $X_1$, $X_2$, $Y_1$, and $Y_2$ are as defined in Formula 1 above.

Examples of hydroxycucurbituril and its mother cucurbituril used as a synthetic material for the compound of Formula 2 above are disclosed together with their structural formulae and synthetic methods in Korean Patent Application Nos. 02-68362, 02-318, 01-57573, 01-39756, and 00-33026, filed by the present applicants, the disclosures of which are incorporated herein by reference in their entireties.

The compound of Formula 3 can thread through the cucurbituril derivative of Formula 2. An end of the compound of Formula 3 has a functional group for immobilization to a solid substrate and the other end has a functional group for a linkage with a biomaterial including DNA or protein or a detection material for a sensor.

In the rotaxane compound of Formula 1, X1 and X2 may be each independently secondary ammonium, 1,4-substituted pyridinum, or benzyl ammonium; and Y1 and Y2 may be each independently a primary amine group, an amide group, an acrylamine group, an alkylester group, an aldehyde group, a carboxyl group, an alkoxysilane group, a halogenated acyl group, a hydroxyl group, a thiol group, a halogen group, a cyan group, an isocyan group, or an isothiocyan group.

Preferably, the rotaxane compound of Formula 1 is selected from compounds represented by Formulae 5 through 13:

<Formula 5>
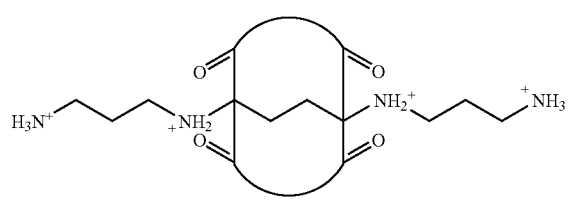

<Formula 6>
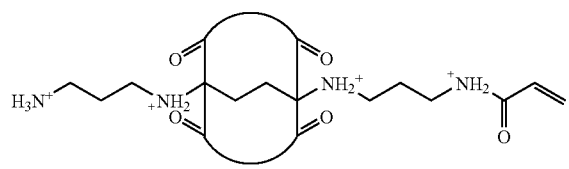

<Formula 7>
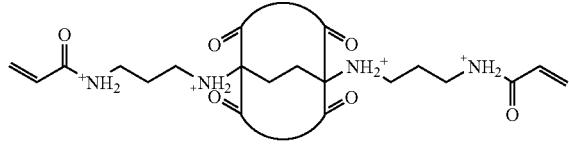

<Formula 8>
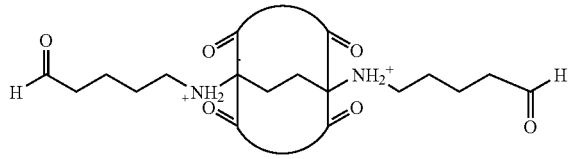

<Formula 9>
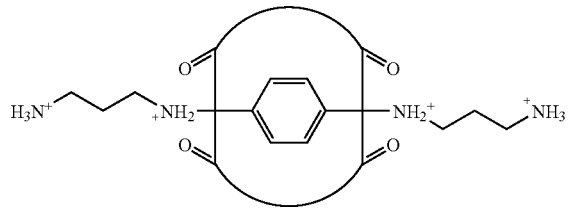

-continued

<Formula 10>
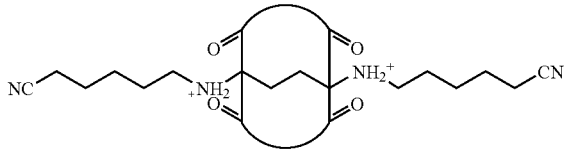

<Formula 11>
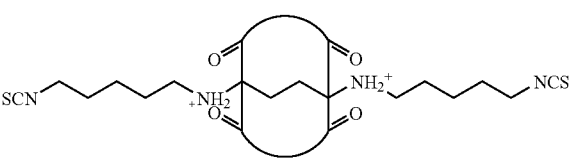

<Formula 12>
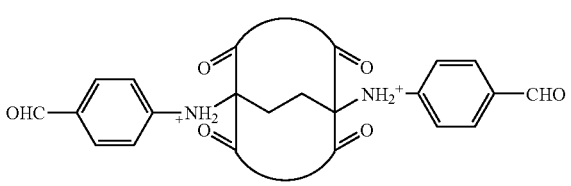

<Formula 13>
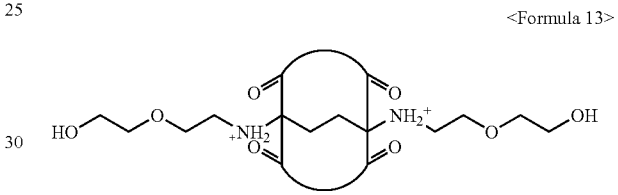

The rotaxane compound of Formula 1 may be prepared as follows.

The compound of Formula 3 synthesized by a common organic synthetic method known in the pertinent art and the compound of Formula 2 synthesized by a method disclosed in Korean Patent Application Nos. 02-68362, 02-318, 01-57573, 01-39756, or 00-33026, filed by the present applicants, are dissolved in water, dimethylformamide, or diemethylsulfoxide, to prepare the compound of Formula 1 by self-assembling of the compound of Formula 2 and the compound of Formula 3.

The rotaxane compound of Formula 1 can be bonded to a modified solid substrate with various end functional groups to form a desired solid substrate.

The compound of Formula 1 may be bonded to the solid substrate in a density of 0.05-0.5 compounds/nm2. The solid substrate may be a glass, a silicon wafer, an indium tin oxide (ITO) glass, an aluminum oxide substrate, or a titanium dioxide substrate.

In the modified solid substrate bonded with the rotaxane compound of Formula 1, rotaxane molecules constituting a linkage layer can be spaced apart from each other by a predetermined distance. The spacing between the molecules within the linkage layer is determined according to the type of cucurbituril or its derivative of Formula 2 constituting the compound of Formula 1.

The solid substrate bonded with the rotaxane compound of Formula 1 can be used in preparation of a gene chip.

The solid substrate bonded with the rotaxane compound of Formula 1 can also be used in preparation of a protein chip or a sensor for biomaterial assay.

The gene chip, the protein chip, and the sensor for biomaterial assay prepared using the solid substrate bonded with the rotaxane compound of Formula 1 have a linkage layer on which rotaxane molecules are spaced apart from each other by a predetermined distance. Therefore, biomaterials, such as genes and proteins, immobilized on the linkage layer can also be spaced regularly. Furthermore, the rotaxane compound of Formula 1 within the linkage layer of the solid substrate for a biochip has fewer functional groups that can form a nonspecific bond such as a hydrogen bond with a biomaterial to be immobilized on the linkage layer, which makes the present invention more practical.

Hereinafter, the present invention will be described more specifically with reference to the following examples. However, the following examples are provided only for illustrations and thus the present invention is not limited to or by them.

Example 1

Preparation of Rotaxane Compound 180 mg (0.5 mmol) of spermine tetrachloride of Formula 4 was dissolved in 10 ml of water and 500 mg (0.5 mmol) of cucurbit[6]uril (CB[6]) was added thereto. The reaction mixture was filtered with a membrane filter and 340 mg (2 mmol) of ammonium hexafluorophosphate was added to the filtrate. The resultant precipitate was filtered with a membrane filter and dried to give a compound of Formula 5.

Example 2

Preparation of Rotaxane Compound 1.03 g (0.58 mmol) of the compound of Formula 5 was dissolved in 50 ml of dimethylformamide. 395 ml (4.62 mmol) of acryloyl chloride and 348 ml (2.32 mmol) of triethylamine were added thereto and stirred. After the reaction terminated, a saturated aqueous solution of tetrabutylammonium chloride was added and the resultant precipitate was filtered with a membrane filter, followed by drying, to give a compound of Formula 6.

<Formula 6>

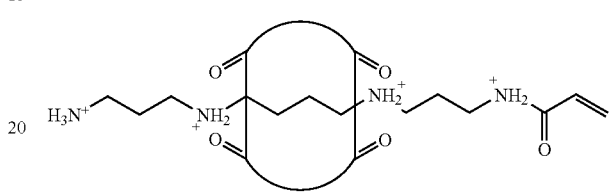

Example 3

Preparation of Solid Substrate and Density Measurement of Introduced Amine Groups A glass substrate was washed with a piranha solution (a 3:1 mixture of sulfuric acid and hydrogen peroxide) to introduce a hydroxyl group to a surface of the glass substrate and then placed in a 10 ml vial under a nitrogen atmosphere. Then, a 10 mM toluene solution of (3-isocyanpropyl)triethoxysilane was added thereto and incubated at room temperature to perform silanization.

After the silanization was completed, the glass substrate was washed with toluene and vacuum dried. A solution of the compound of Formula 5 of Example 1 in dimethylformamide and 4 equivalents of triethylamine were added and stirred at room temperature under a nitrogen atmosphere. Then, the glass substrate was washed with anhydrous dimethylformamide, immersed in a solution of ethanolamine in anhydrous dimethylformamide to remove the reactivity of residual isocyanated silane, and washed with diluted hydrochloric acid, to give a solid substrate of Formula 14:

<Formula 4>

<Formula 5>

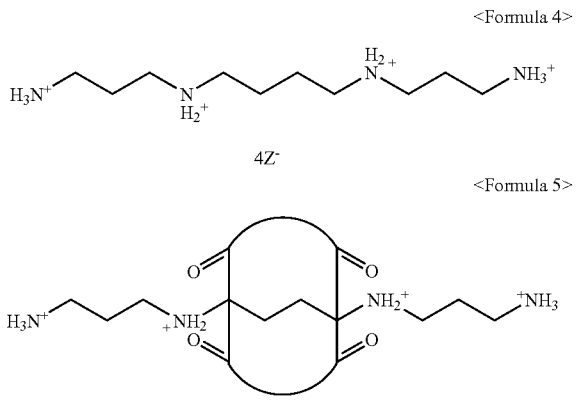

<Formula 14>

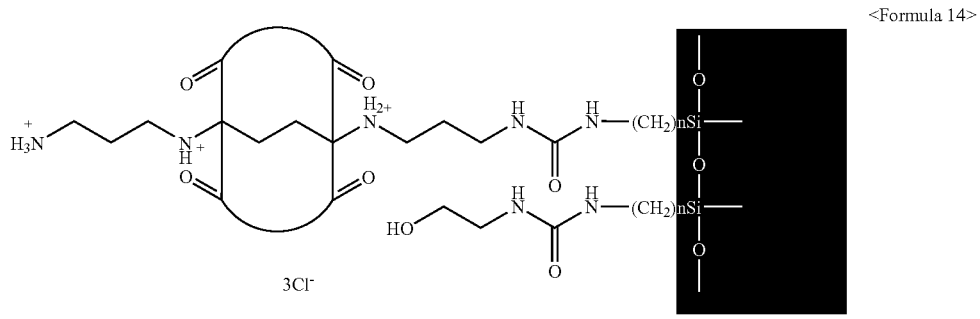

The density of amine groups present on the glass substrate of Example 3 was measured using the fluorescence of 9-anthraldehyde. At this time, a density measurement using 9-anthraldehyde is based on a smaller size of 9-anthradehyde than CB[6] of Formula 1 [Langmuir, 19, 2003, p 2357].

According to the measurement result, the amine groups present on the surface of the glass substrate of Example 3 exhibited the surface density of 0.1 amines/nm$^2$.

Example 4

Preparation of Solid Substrate and Density Measurement of Introduced Amine Groups A glass substrate was washed with a piranha solution to introduce a hydroxyl group to a surface of the glass substrate and then placed in a 10 ml vial under a nitrogen atmosphere. Then, a 10 mM toluene solution of (3-aminopropyl)triethoxysilane was added thereto and incubated at room temperature to perform silanization.

After the silanization was completed, the glass substrate was washed with toluene and heated at 120° C. under a reduced pressure for one hour. The glass substrate was cooled, immersed in a solution of phenyl 1,4-diisothiocyanate in anhydrous dimethylformamide, and stirred at room temperature under a nitrogen atmosphere.

The glass substrate was thoroughly washed, a solution of the compound of Formula 5 of Example 1 in anhydrous dimethylformamide and 4 equivalents of triethylamine were added thereto and stirred at room temperature under a nitrogen atmosphere. Then, the glass substrate was thoroughly washed with anhydrous dimethylformamide, immersed in a solution of ethanolamine in anhydrous dimethylformamide to remove the reactivity of residual isothiocyanated silane, and washed with diluted hydrochloric acid, to give a solid substrate of Formula 15:

The density of amine groups present on the glass substrate of Formula 15 thus prepared was measured in the same manner as in Example 3.

According to the measurement result, the amine groups present on the surface of the glass substrate of Formula 15 exhibited the surface density of 0.1 amines/nm$^2$.

Example 5

Preparation of Solid Substrate and Density Measurement of Introduced Amine Groups A glass substrate was washed with a piranha solution to introduce a hydroxyl group to a surface of the glass substrate and then added in a 10 ml vial under a nitrogen atmosphere. Then, a 10 mM toluene solution of (3-thiolpropyl)triethoxysilane was added thereto and incubated at room temperature to perform silanization.

After the silanization was completed, the glass substrate was thoroughly washed with toluene, added to an aqueous solution of the compound of Formula 6 of Example 2, and stirred at room temperature. The glass substrate was thoroughly washed with distilled water, immersed in a solution of acrylonitrile in dimethylformamide to remove residual reactivity, and washed with dimethylformamide and methanol, to give a solid substrate of Formula 16:

<Formula 15>

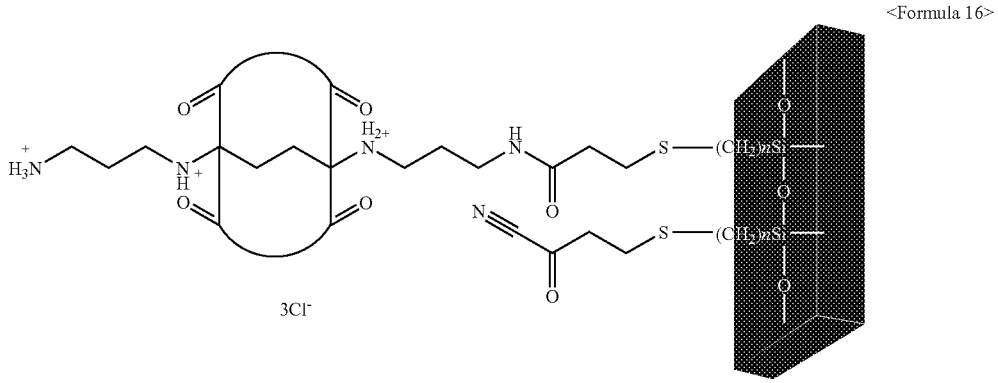

<Formula 16>

The density of amine groups present on the glass substrate of Formula 16 was measured in the same manner as in Example 3. According to the measurement result, the amine groups present on the surface of the glass substrate of Formula 16 exhibited the surface density of 0.1 amines/nm2.

From the density measurement results, it can be seen that the density of the amine groups present on the solid substrates prepared in Examples 3 through 5 was remarkably reduced, relative to that of an aminosilane-modified glass substrate. Considering that the diameter of double-stranded DNA is about 2 nm, since 0.4 amines correspond to a single DNA, the glass substrates of Examples 3 through 5 would not cause a steric hindrance during DNA hybridization. Furthermore, according to a method reported by Georgiadis et al., the density of amine groups present on a solid substrate is about 0.01 amines/nm2. In this regard, the density of the amine groups on the solid substrate of the present invention is 10 times higher than that of the conventional solid substrate. Therefore, enhanced detection sensitivity is anticipated.

As is apparent from the above description, a rotaxane compound of the present invention allows for the uniform spacing between rotaxane molecules within a linkage layer formed on a solid substrate. Therefore, a biochip with superior selectivity and sensitivity can be produced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A solid substrate for a biochip comprising a compound represented by Formula 1 below:

(1)

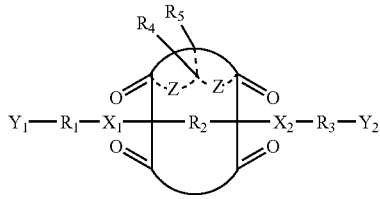

wherein $R_1$, $R_2$, and $R_3$ are each independently saturated or unsaturated linear $C_2$-$C_{10}$ alkylene, ethyleneglycol oligomer, 1,4-substituted benzene, or 1,4-substituted pyridine; $R_4$ and $R_5$ are each independently hydrogen, an alkenyloxy group with an unsaturated bond end and a substituted or unsubstituted alkyl moiety of $C_1$-$C_{20}$, a carboxyalkylsulfinyloxy group with a substituted or unsubstituted alkyl moiety of $C_1$-$C_{20}$, a carboxyalkyloxy group with a substituted or unsubstituted alkyl moiety of $C_2$-$C_8$, an aminoalkyloxy group with a substituted or unsubstituted alkyl moiety of $C_2$-$C_8$, or a hydroxyalkyloxy group with a substituted or unsubstituted alkyl moiety of $C_2$-$C_8$; $X_1$ and $X_2$ are each independently a positively charged functional group for ion-dipole interaction with an oxygen atom of cucurbituril or its derivative of represented by Formula 2; $Y_1$ is a functional group for a linkage with a biomaterial comprising a gene or a protein; and $Y_2$ is a functional group capable of binding to the solid substrate, wherein the compound of Formula 1 bonded to the solid substrate provides a linkage layer with a predetermined spacing in the biochip; and wherein a compound of Formula 3

$$Y_1-R_1-X_1-R_2-X_2-R_3-Y_2 \qquad (3)$$

(wherein $R_1$, $R_2$, $R_3$, $X_1$, $X_2$, $Y_1$, and $Y_2$ are as defined in Formula 1 above)

vertically passes through a cavity of cucurbituril or its derivative represented by Formula 2

(2)

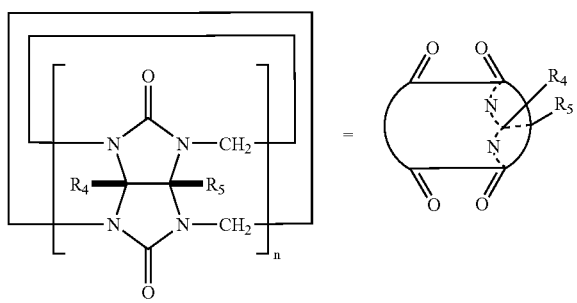

(wherein n is an integer of 4 to 20; and $R_4$ and $R_5$ are as defined in Formula 1 above).

2. The solid substrate of claim 1, wherein $X_1$ and $X_2$ are each independently secondary ammonium, 1,4-substituted pyridinum, or benzyl ammonium; and $Y_1$ and $Y_2$ are each independently a primary amine group, an amide group, an acrylamine group, an alkylester group, an aldehyde group, a carboxyl group, an alkoxysilane group, a halogenated acyl group, a hydroxyl group, a thiol group, a halogen group, a cyan group, an isocyan group, or an isothiocyan group.

3. The solid substrate of claim 1, wherein the compound of Formula 1 is selected from the group consisting of compounds represented by Formulae 5 through 13:

(5)
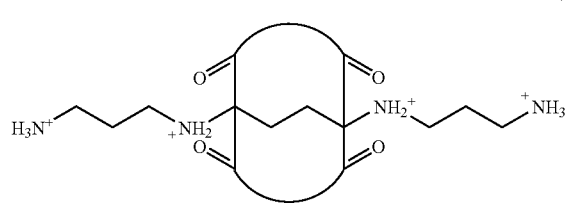

(6)
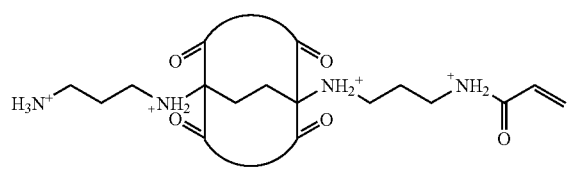

(7)
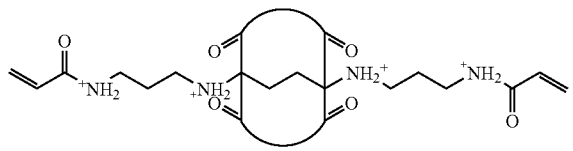

(8)
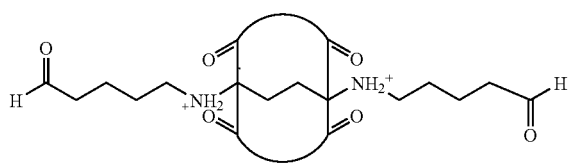

(9)
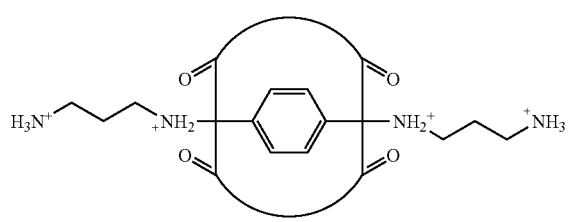

(10)
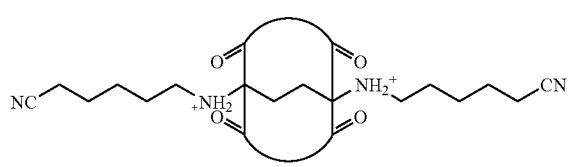

-continued

(11)

(12)
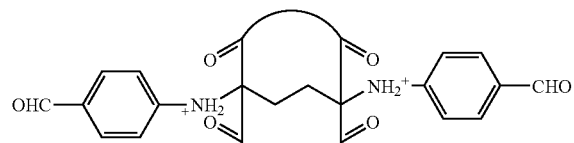

(13)
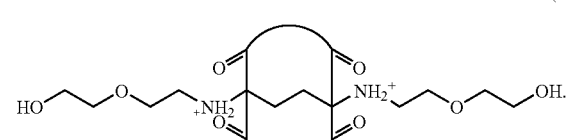

4. The solid substrate of claim 1, wherein the compound of Formula 1 is present in a density of 0.05 to 0.6 compounds/nm$^2$.

5. The solid substrate of claim 1, which is a glass, a silicon wafer, an indium tin oxide (ITO) glass, an aluminum oxide substrate, or a titanium dioxide substrate.

6. A gene chip comprising the solid substrate of claim 1 and a DNA capable of selectively interacting with a DNA to be assayed.

7. A protein chip comprising the solid substrate of claim 1 and a protein capable of selectively interacting with a protein to be assayed.

8. A sensor for biomaterial assay comprising the solid substrate of claim 1, wherein the biomaterial is a DNA or protein.

9. The solid substrate of claim 1, wherein the biochip is selected from the group consisting of a gene chip, a protein chip and a sensor for biomaterial assay.

10. The solid substrate of claim 1, wherein the compound of Formula 1 is bonded to the solid substrate via a covalent bond or a non-covalent bond.

\* \* \* \* \*